(12) United States Patent
Celi et al.

(10) Patent No.: US 9,000,790 B2
(45) Date of Patent: Apr. 7, 2015

(54) DEFECT DETECTION BY THERMAL FREQUENCY IMAGING

(75) Inventors: Guillaume Celi, Grenoble (FR);
Thierry Parrassin, Grenoble (FR);
Sylvain Dudit, Meylan (FR)

(73) Assignee: STMicroelectronics SA, Montrouge (FR)

( * ) Notice: Subject to any disclaimer, the term of this patent is extended or adjusted under 35 U.S.C. 154(b) by 425 days.

(21) Appl. No.: 13/568,020

(22) Filed: Aug. 6, 2012

(65) Prior Publication Data

US 2013/0002283 A1 Jan. 3, 2013

(30) Foreign Application Priority Data

May 8, 2011 (FR) ...................... 11 57175

(51) Int. Cl.
*G01R 31/308* (2006.01)
*G01R 31/311* (2006.01)
*G01N 21/17* (2006.01)
*G01N 21/55* (2014.01)

(52) U.S. Cl.
CPC .......... *G01R 31/311* (2013.01); *G01N 21/1717* (2013.01); *G01N 21/55* (2013.01); *G01N 2021/1731* (2013.01); *G01N 2021/1753* (2013.01); *G01N 2021/1765* (2013.01)

(58) Field of Classification Search
None
See application file for complete search history.

(56) References Cited

U.S. PATENT DOCUMENTS

| 6,407,560 | B1 * | 6/2002 | Walraven et al. | ........ 324/754.23 |
| 6,444,895 | B1 * | 9/2002 | Nikawa | ......................... 136/212 |
| 6,549,022 | B1 * | 4/2003 | Cole et al. | ................ 324/754.23 |
| 8,754,633 | B2 * | 6/2014 | Ng et al. | ......................... 324/97 |
| 2007/0046301 | A1 * | 3/2007 | Kasapi | ......................... 324/751 |
| 2010/0327875 | A1 * | 12/2010 | Patterson | ..................... 324/501 |

* cited by examiner

*Primary Examiner* — Arleen M Vazquez
*Assistant Examiner* — Feba Pothen
(74) *Attorney, Agent, or Firm* — Slater & Matsil, L.L.P.

(57) ABSTRACT

A method can be used for detecting defects in an electronic integrated circuit that includes a power input and a data input. The electronic integrated circuit is powered with a periodic power signal having a frequency and an input signal is applied to the data input. A surface of the electronic integrated circuit is swept with a laser beam. A first image is generated using a laser beam reflected from the surface and a second image is generated using a selected part of the laser beam reflected from the surface. The selected part of the reflected laser beam has a frequency that corresponds to the frequency of the power signal. Defects in the integrated circuit can be detected by superposing the first image and the second image.

25 Claims, 3 Drawing Sheets

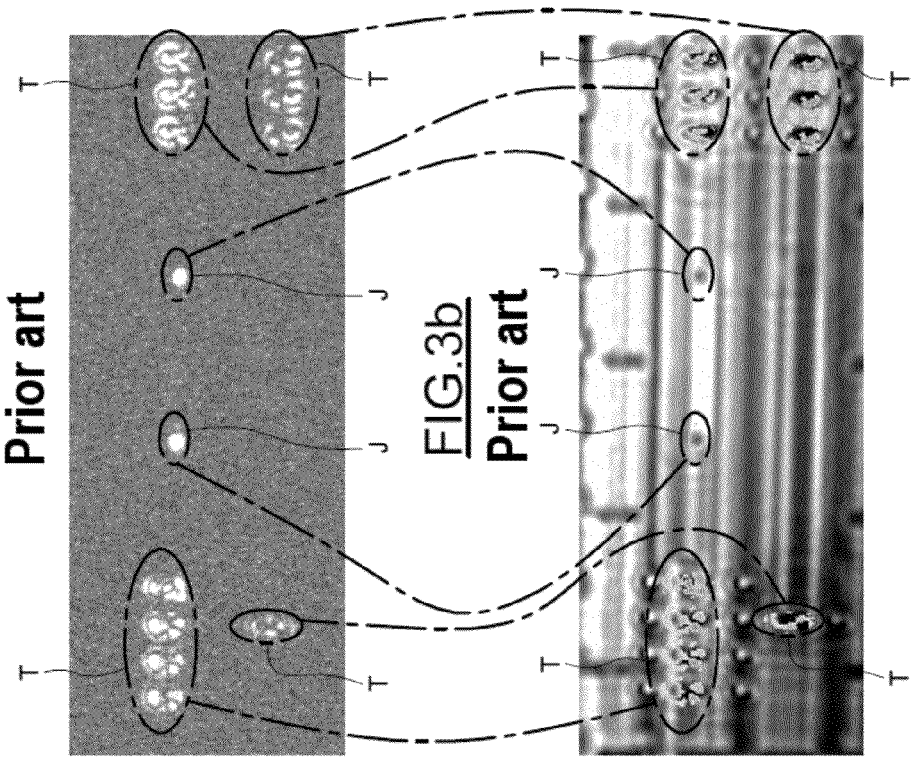
FIG.3a Prior art
FIG.3b Prior art
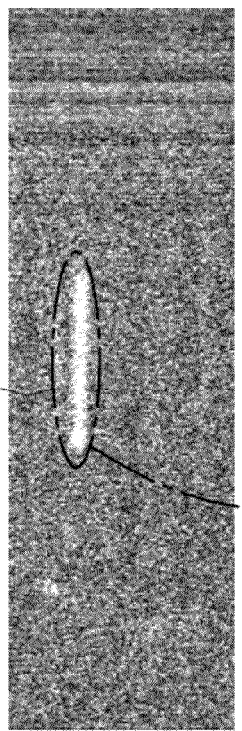
FIG.2a
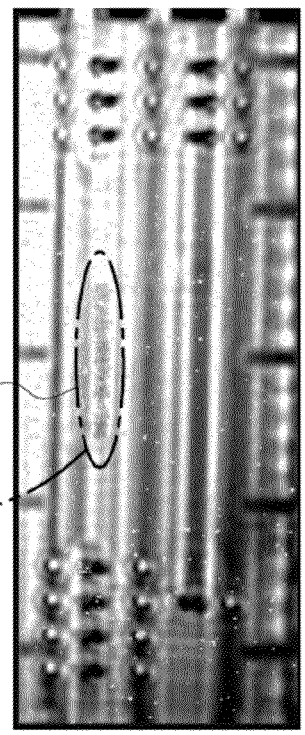
FIG.2b

DEFECT DETECTION BY THERMAL FREQUENCY IMAGING

This application claims priority to French Patent Application 1157175, which was filed Aug. 5, 2011 and is incorporated herein by reference.

TECHNICAL FIELD

The invention relates to the detection of defects in an electronic integrated circuit, and in particular embodiments to detection of defects via structural analysis using a reflected light beam.

BACKGROUND

Several techniques are used to detect defects possibly present in an electronic integrated circuit. One of these techniques, called laser voltage imaging (LVI), analyzes a laser beam reflected by the circuit. To do this, the surface of the circuit is swept by a laser beam while the circuit is powered with a continuous signal and while a periodic test signal is delivered to the data input of the circuit. The reflected laser beam is then measured and delivered, on the one hand, to an imager capable of producing a map of the surface of the circuit using the intensity of the reflected laser beam, and, on the other hand, to a spectrum analyzer performing a frequency analysis targeted on the frequency of the test signal, allowing the frequencies present to be mapped onto the surface of the circuit and possible frequency signatures to be detected.

The frequency signatures correspond to an intensity peak for a given frequency, in this case the test frequency, in the reflected laser beam.

The imager produces an image using the variation in intensity of the reflected laser beam. The image thus produced comprises dark regions and lighter regions making it possible to discern, in the image, the location of the various electronic components. The spectrum analyzer only measures the intensity of the reflected laser beam at the frequency of the test signal and thus determines in which locations on the electronic integrated circuit the maximum intensity was reflected at the frequency of the test signal.

This known technique thus allows specific available frequencies to be mapped onto active regions of the electronic integrated circuit. It uses the properties of the materials, and more particularly the variation in the charge density within the materials.

However, employing LVI on its own does not allow the defective electronic components to be reliably and precisely located. This is because, LVI employs a periodic test signal and a spectrum analyzer centered on the frequency of the test signal. This configuration results in a frequency-signature map corresponding both to defective electronic components and to functioning switches or transistors. This is because functioning transistors show charge densities modulated at the frequency of the test signal, and the transistors also heat up at this same frequency. Consequently, the spectrum analyzer centered on the test frequency outputs a signature frequency both for functioning transistors, which heat up or modulate charge density at the test frequency, and for defective electronic components, which heat permanently. It is therefore not possible to differentiate between the frequency signatures of transistors that are functioning normally and the frequency signatures of defective components.

SUMMARY OF THE INVENTION

In one embodiment and implementation, a method and associated system are provided for detecting defects in an electronic integrated circuit, allowing defective electronic components in the electronic integrated circuit to be reliably and precisely located, and more particularly allowing the frequency signatures due to defective components in the integrated circuit to be differentiated from the frequency signatures corresponding to functioning transistors.

According to one aspect, in one implementation, a method is provided for detecting defects in an electronic integrated circuit possessing a power input and at least one data input According to one general feature, the method comprises:

a. powering the integrated circuit with a periodic power signal;
b. supplying an input signal to the data input;
c. sweeping the surface of the integrated circuit with a laser beam;
d. receiving the reflected laser beam;
e. selecting the part of the reflected laser beam having a frequency corresponding to the frequency of the power signal;
f. generating a first image using the reflected laser beam and generating a second image using the selected part of the reflected laser beam; and
g. detecting defects in the integrated circuit by superposing the first image and the second image.

The laser beam reflected by the electronic integrated circuit is modulated inter alia by the charge density present in the material and by the reflectance of the material, i.e., the ability of the material to reflect.

Regarding the reflectance, the intensity of the laser beam reflected by the material, i.e., the amount of light reflected by the material, is given by its reflectivity $\phi_0 R$, where $\phi_0$ is the intensity of the laser beam emitted and R is the reflectivity coefficient of the material of the electronic component.

When the temperature of a material changes, the reflectivity coefficient is also modified and the intensity of the reflected laser beam becomes:

$$\phi_0(R \pm \Delta R)$$

The relation between the reflectivity coefficient and the temperature of the material is therefore:

$$\frac{\Delta R}{R} = \frac{1}{R}\frac{\partial T}{\partial T}\Delta T$$

The temperature of defective electronic components increases when they are powered and the intensity of the reflected laser beam differs from when the defective electronic component is not powered.

Since the integrated circuit is powered by a periodic power signal, the temperature of the defective electronic components varies periodically with the power signal. The intensity of the laser beam reflected from the defective electronic components, depending on the reflectivity of the materials, is therefore modulated as a function of the temperature variation, which is modulated as a function of the frequency of the power signal. The intensity of the laser beam reflected by the defective components therefore corresponds to $\phi_0(R+\tau\Delta R)$, where $\tau$ is the heating time constant of the material of the electronic component.

The defective components will therefore be heated at a frequency corresponding to the frequency $f_{alim}$ of the power signal. By generating a second image using the selected part of the reflected laser beam, an image comprising located frequency signatures, possibly corresponding to defective electronic components, is obtained.

Since the power signal is a periodic signal, the input signal may be a zero or non-zero continuous signal, in contrast will the LVI technique in which the test signal is necessarily a periodic signal. This is because, since the power signal is periodic, the defective components will heat up at the power frequency $f_{alim}$ of the power signal. A spectrum analyzer used to select the part of the reflected laser beam possessing the power frequency $f_{alim}$ will therefore observe the defective components heating up at the power frequency $f_{alim}$, whether the test signal is a zero or non-zero continuous signal or a periodic signal.

Preferably, the input signal is a periodic signal, and the frequency of the power signal is different from the frequency of the input signal.

By powering the power circuit with a power signal the frequency of which is different from the frequency of the test signal, defective electronic components heat up at a frequency different from the operating frequency of the transistors of the integrated circuit. Thus, the selected part of the reflected laser beam with a frequency corresponding to the frequency of the power signal does not contain frequency signatures corresponding to the normally functioning transistors. Only frequency signatures due to the heat-up of defective components, which will be referred to as thermal signatures, may be seen in the selected part of the reflected laser beam.

Advantageously, the frequency of the power signal may be different from the first five harmonics of the frequency of the input signal.

In this way, the probability of obtaining frequency signatures due to functioning transistors, which will be referred to as parasitic signatures, in the second image is greatly reduced.

Preferably, the power signal is a square-wave signal. Using a square-wave signal to power the electronic integrated circuit, rather than a sinusoidal signal for example, allows the heating of the defective electronic components to be optimized, i.e., it makes it possible for the heat-up time of an electronic component to correspond to the heating time constant of the material of the electronic component, rather than to a longer time. Specifically, with a square-wave power signal, the voltage passes instantaneously from a minimum value to a maximum value, causing the electronic components to heat up more rapidly than in the case where a sinusoidal or triangular power signal is used, for example.

Preferably, the half-period of the power signal is longer than the longest heating time constant of the component materials of the electronic elements of the integrated circuit.

Thus, there is enough time for the component materials of the electronic elements to heat up completely in a half-period and to cool down completely in the other half-period. If the half-period of the power signal is shorter than the longest heating time constant of the component materials of the electronic elements, there is not enough time for a defective electronic element to heat up completely, or to cool down completely. Its temperature oscillation is then of a small, even almost zero, amplitude, and the intensity of the reflected laser beam is not, or only weakly, modulated by the temperature, preventing detection of a frequency signature corresponding to a thermal signature of a defective electronic element.

The frequency of the power signal preferably lies between 10 kHz and 1 MHz. For power-signal frequencies higher than 1 MHz, the heating time constant of the component materials of the electronic elements is generally longer than the half-period of the power signal, and the materials of the defective electronic elements do not have enough time to heat up and are more difficult to detect.

For power-signal frequencies lower than 10 kHz, the signal-to-noise ratio is reduced, preventing clear observation of thermal signatures and therefore making defect detection even more difficult.

Advantageously, steps a) to g) may be repeated for various power-signal frequencies. For example, by repeating these steps for various frequencies above 10 KHz with a duty cycle of ½, the intensity of the thermal signatures of the defective electronic components may be made to vary. This is because the intensity of the signatures is higher at lower frequencies and lower at higher frequencies, if the signature is a thermal signature. Thus, if the intensity of a frequency signature does not vary, the frequency signature is not a thermal signature but an LVI-type parasitic signature and the electronic component is not defective but probably corresponds to a normally functioning transistor or to a non-thermal defect.

According to the same principle, it is possible to repeat steps a) to g) while modifying the duty cycle of the power signal for a given frequency, i.e., for a square-wave signal for example, by modifying the on-time relative to the off-time. By repeating these steps for various power-signal duty cycles while holding the frequency constant, the intensity of the frequency signature obtained in the second image is made to vary depending on the frequency-signature type. If the intensity of the frequency signature increases at low frequencies when the duty cycle of the power signal is changed, the frequency signature corresponds to a thermal signature related to the heating of a defective electronic component. However, if the intensity of the frequency signature does not change or decreases when the duty cycle of the power signal is modified, the frequency signature does not correspond to a thermal signature but to a parasitic signature due to a functioning transistor or to a non-thermal defect.

According to another aspect, in one embodiment, a system is provided for detecting defects in an integrated circuit possessing a power input and at least one data input.

According to a general feature, the system comprises a periodic signal generator that generates a periodic signal and is connected to the power input. An input signal generator can generate an input signal at the data input. A laser is able to generate a laser beam. A mechanism is provided to move the laser beam and the integrated circuit relative to each other so as to sweep the laser beam over the surface of the integrated circuit and a sensor is able to receive the reflected laser beam and deliver an output signal. A frequency analyzer can select part of the output signal having a frequency corresponding to the frequency of the power signal and a processor is configured to generate a first image using the output signal and a second image using the part of the output signal, and to detect defects by superposing the first image and the second image.

The input signal generator may advantageously comprise a signal generator generating a zero or non-zero continuous signal.

Alternatively, the input signal generator may comprise a signal generator generating a periodic signal. The frequency of the power signal being different from the frequency of the input signal.

Preferably, the periodic signal generator is configured to deliver a power signal the frequency of which is different from the first five harmonics of the periodic signal delivered by the input signal generator.

The periodic signal generator preferably generates a square-wave signal.

The circuit comprises electronic elements, and the periodic signal generator is preferably configured to deliver a power signal the half-period of which is longer than the longest heating time constant of the component materials of the electronic elements.

The periodic signal generator may advantageously be a variable frequency and/or variable duty-cycle generator able to generate a periodic signal having a frequency lying between 10 kHz and 1 MHz.

BRIEF DESCRIPTION OF THE DRAWINGS

Other advantages and features of the invention will become clear on examining the detailed description of one non-limiting implementation and embodiment, and the appended drawings in which:

FIGS. 2a and 2b illustrate, respectively, an exemplary second image generated using the selected part of the reflected laser beam, the frequency of the selected part corresponding to the frequency of the power signal, and an example of the superposition of the first image and the second image, according to one embodiment of the invention;

FIGS. 3a and 3b illustrate, respectively, an exemplary second image generated using the selected part of the reflected laser beam, the frequency of the selected part corresponding to the frequency of the input signal, and an example of the superposition of the first image and the second image, according to the prior art.

DETAILED DESCRIPTION OF ILLUSTRATIVE EMBODIMENTS

Figure 1:
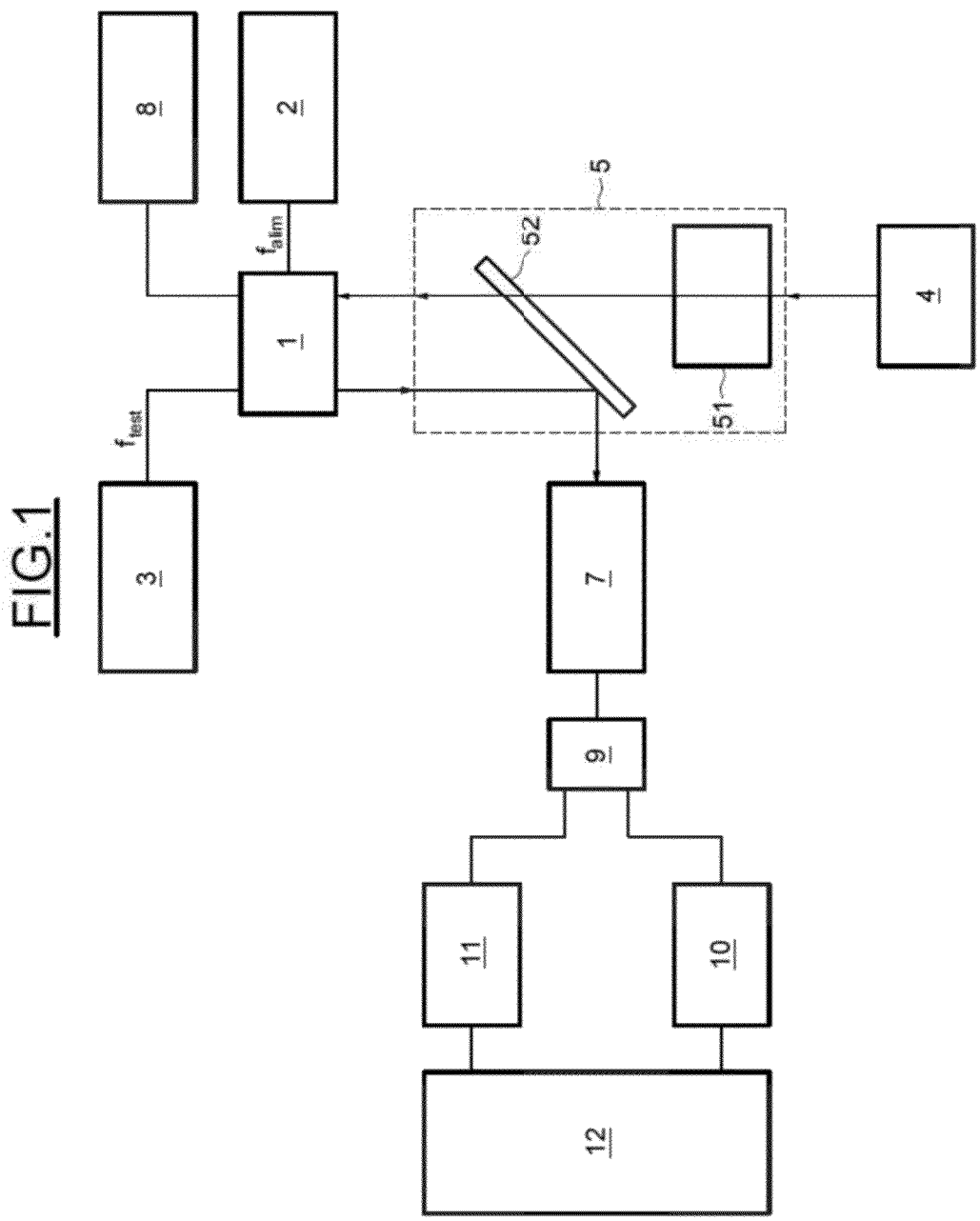
FIG. 1 shows an exemplary embodiment of a system for detecting defects in an electronic integrated circuit.

FIG. 1 shows a diagram of an exemplary system for detecting defects in an electronic integrated circuit 1 according to one embodiment.

The power input of the integrated circuit 1 is connected to a generator 2 that delivers a periodic power signal at a power frequency $f_{alim}$, and the data input of the circuit is connected to test signal generator 3, which generates a test signal. The test signal may be a zero or non-zero continuous signal or a periodic signal, such as a square-wave signal for example, having a test frequency $f_{test}$. The periodic power signal delivered by the generator 2 is, for example, a square-wave signal oscillating between a minimum potential and a maximum potential at a power frequency $f_{alim}$ different from the test frequency $f_{test}$ and from the first five harmonics of the test frequency $f_{test}$. The maximum potential of the power signal generally corresponds to a nominal operating voltage $V_{DD}$, and the minimum potential corresponds to 60% of this nominal operating voltage $V_{DD}$.

A laser 4 delivers a laser beam to an optical assembly 5 allowing the laser beam to be focused onto the surface of the circuit 1. The laser 4 used may be a tunable, continuous-wave or pulsed, laser for example.

The electronic integrated circuit 1 is prepared beforehand in order to be compatible with the optical assembly 5 of the detection system. To do this, the back side is thinned by polishing or opaque materials may even be removed from the front side.

The optical assembly 5 comprises optical elements 51 allowing the laser beam to be focused and conditioned with the desired properties, especially a set of treated or untreated lenses allowing the beam to be focused on the region of interest on the back side or front side of the integrated circuit 1. Optical assembly 5 also comprises an optical element 52 that transmits the incident laser beam and reflects the laser beam reflected by the surface of the electronic integrated circuit 1 onto a photosensitive sensor 7.

The surface of the integrated circuit 1 is swept with the laser beam by way of a moving mechanism 8 thereby allowing the circuit 1 to be moved in a plane orthogonal to the direction of the laser beam. It is also possible to replace the moving mechanism 8 with a moving mechanism for the laser 4 and the optical assembly 5 or a mechanism for deflecting the incident laser beam. In these latter examples, the integrated circuit 1 could remain stationary.

The photosensitive sensor 7 receives the reflected laser beam and delivers an output signal to duplicator 9, which duplicates the output signal and delivers the output signal to a spectrum analyzer 10, on the one hand, and to an amplifier 11, on the other.

The spectrum analyzer 10 amplifies the received signal and selects a part of the output signal that has a frequency corresponding to the power frequency $f_{alim}$ of the power signal. The spectrum analyzer 10 then outputs a value corresponding to the total energy measured, i.e., to the intensity, for the selected frequency, making it possible to image frequency signatures having the power frequency $f_{alim}$.

Processor 12, for example a programmed microprocessor, receives as input the output signal amplified by the amplifier 11 and the part of the output signal selected by the spectrum analyzer 10.

The processor 12 then generates a first image using the output signal, allowing a map of the surface of the integrated circuit with the various electronic components to be obtained, and a second image using the selected part of the output signal, allowing frequency signatures to be revealed. Examples of the images are shown in the thermal signatures illustrated in FIG. 2a.

The superposition of the first image and the second image allows the defective electronic element or elements R to be identified and located in the integrated circuit 1, as illustrated in FIG. 2b.

FIGS. 3a and 3b illustrate an exemplary second image and an example of the superposition of a first image and a second image according to the prior art and more particularly using an LVI (laser voltage imaging) detection system. The frequency signatures revealed in FIG. 3a correspond to transistors, in the arrays denoted by the reference T, which are functioning normally and are not defective. This is due to the fact that the frequency analyzer used in LVI is set to the frequency of the input signal, and the power signal is a continuous signal. Two signatures may also be seen at junctions J of the defective resistor, but it is not possible, from the superposition of images in FIG. 3b, to deduce which electronic components are defective.

However, it will be noted that FIGS. 2a and 2b (FIG. 2a illustrating the second image and FIG. 2b illustrating the superposition of the first image and the second image, according to one embodiment of the invention) clearly show only a single frequency signature, namely a thermal signature, corresponding to the heat-up of the defective electronic element, which in this case is a resistor R. In this embodiment and implementation, the frequency selected by the frequency analyzer is the power frequency $f_{alim}$, which is different from the test frequency $f_{test}$ of the test signal and to the first five harmonics of the frequency of the test signal. Thus, the parasitic signatures, due to normally operating transistors, which appear with LVI (FIGS. 3a and 3b) do not appear in this embodiment and implementation.

Figure 4:
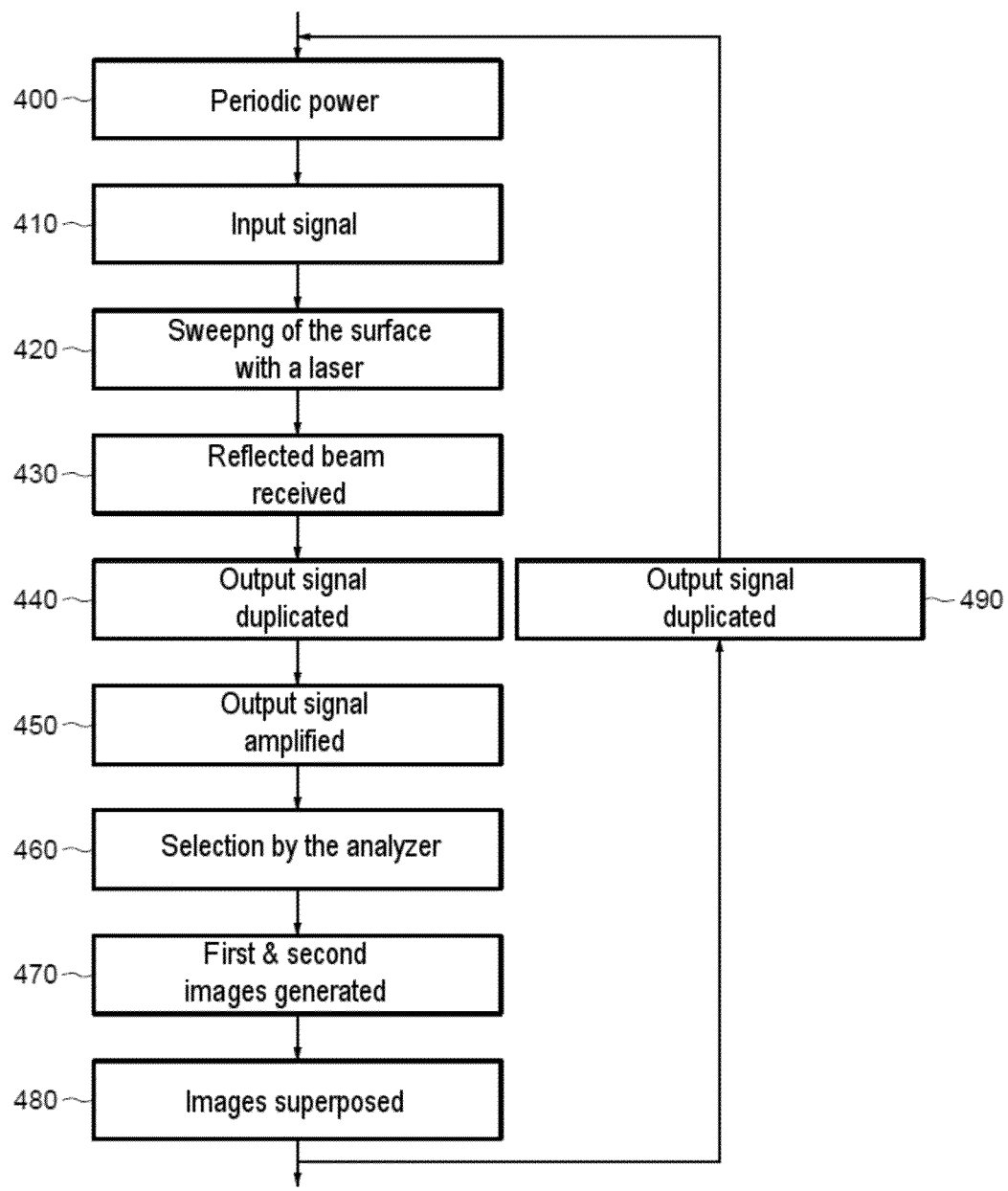
FIG. 4 shows a flow diagram of an exemplary implementation of a method for detecting defects in an integrated circuit.

FIG. 4 presents a flow chart of an exemplary implementation of a method for detecting a defect in an integrated circuit 1 comprising a power input and a data input.

In a first step 400 the integrated circuit 1 is powered with a periodic square-wave power signal having a power frequency $f_{alim}$ above 10 kHz and preferably below 1 MHz. The half-period of the power signal is longer than the longest heating time constant τ of the component materials of the electronic elements of the integrated circuit 1.

In a following step 410, a test signal is delivered to the data input of the integrated circuit 1. The test signal is a periodic signal and the power frequency $f_{alim}$ is different to the test frequency $f_{test}$ of the test signal and from the first five harmonic frequencies of the test signal $f_{test}$.

In a following step 420, the surface of the integrated circuit 1 is swept with a focused laser beam so as to map the entire area of the integrated circuit 1. The integrated circuit 1 may be illuminated either from the back side or front side, depending on the embodiment. The electronic integrated circuit is prepared beforehand in order to remove elements that could prevent the laser beam from accessing electronic elements on the surface of the integrated circuit 1.

In a step 430, the laser beam reflected by the integrated circuit 1 during the sweep is received by the photosensitive sensor 7, which sensor delivers a corresponding electrical output signal to the duplicator 9, for duplicating the output signal in a step 440.

A first duplicate of the output signal is then delivered to an amplifier 11 in a step 450, and a second duplicate of the output signal is delivered to a spectrum analyzer 10 in a step 460. The spectrum analyzer 10 amplifies the second duplicate of the output signal and selects a part of the output signal corresponding to the part of the reflected laser beam possessing a frequency corresponding to the power frequency $f_{alim}$.

In a step 470, the image-generator 12 generates a first image using a first duplicate of the output signal generated by the reflected laser beam, and a second image using the part of the output signal selected by the spectrum analyzer 10.

The first image is generated using the intensity of the laser beam reflected from each point of the integrated circuit 1. The image thus produced comprises dark regions and lighter regions allowing the location of the various electronic elements of the integrated circuit 1 to be seen in the first image.

The second image generated using the signal delivered by the spectrum analyzer having measured the intensity of the reflected laser beam at the power frequency $f_{alim}$ comprises frequency signatures located on the electronic integrated circuit 1.

In a step 480, the two images are superposed in order to detect and localize defective electronic elements on the integrated circuit 1.

In the case where a frequency signature observed in the second image is suspect, it is possible, in a step 490, to modify the power frequency $f_{alim}$ in a frequency range above 10 kHz, and to repeat steps 400 to 480 of the method.

If the intensity of the frequency signature varies with the power frequency $f_{alim}$, and particularly if the intensity of the signature increases at lower frequencies or decreases at higher frequencies, then the frequency signature corresponds to a thermal signature i.e., to a frequency signature due to the heating of a defective electronic component. However, if the frequency signature does not vary when the power frequency $f_{alim}$ is modified, the frequency signature is not a thermal signature but an LVI-type parasitic signature and it is therefore not a defect possessing thermal properties but certainly a normally functioning transistor or a non-thermal defect signature.

In a first variant, it is also possible, after having carried out steps 400 to 480 of the method once, to repeat steps 400 to 480 once at a power frequency $f_{alim}$ above 1 MHz, i.e., with a periodic power signal possessing a half-period shorter than the heating time constant τ of the component materials of the electronic elements. If the frequency signature obtained in the second image disappears, it is highly likely to be a thermal signature due to heating of a defective electronic element and not a parasitic signature due to a normally functioning transistor.

In a second variant, after having carried out steps 400 to 480 of the method once, it is possible to keep the power frequency $f_{alim}$ of the power signal constant but instead modify the duty cycle of the power signal, and then repeat steps 400 to 480.

If the intensity of the frequency signature increases or remains unchanged when the duty cycle of the power signal is modified, the frequency signature corresponds to a thermal signature related to the heating of a defective electronic element. However, if the intensity of the frequency signature decreases when the duty cycle of the power signal is modified, the frequency signature does not correspond to a thermal signature but to an LVI-type parasitic signature due to a functioning transistor or a non-thermal defect.

The method and associated system provided allow defective electronic elements in a circuit to be reliably and precisely detected and located, and more particularly they allow frequency signatures due to defective electronic components in the integrated circuit and frequency signatures corresponding to functioning transistors to be differentiated.

What is claimed is:

1. A method for detecting defects in an electronic integrated circuit that includes a power input and a data input, the method comprising:
   powering the electronic integrated circuit with a periodic power signal having a frequency;
   applying an input signal to the data input;
   sweeping a surface of the electronic integrated circuit with a laser beam;
   generating a first image using a laser beam reflected from the surface;
   generating a second image using a selected part of the laser beam reflected from the surface, the selected part of the reflected laser beam having a frequency corresponding to the frequency of the power signal; and
   detecting defects in the integrated circuit by superposing the first image and the second image.

2. The method according to claim 1, wherein the input signal is a zero or non-zero continuous signal.

3. The method according to claim 1, wherein the input signal is a periodic signal and the frequency of the power signal is different from the frequency of the input signal.

4. The method according to claim 3, wherein the frequency of the power signal is different from the first five harmonics of the frequency of the input signal.

5. The method according to claim 1, wherein the periodic power signal is a square-wave signal.

6. The method according to claim 1, wherein the electronic integrated circuit comprises electronic elements and wherein a half-period of the power signal is longer than a longest heating time constant of materials of the electronic elements.

7. The method according to claim 1, wherein the frequency of the power signal lies between 10 kHz and 1 MHz.

8. The method according to claim 1, further comprising repeating the powering, supplying, sweeping, receiving, selecting, generating and detecting for various power-signal frequencies.

9. The method according to claim 8, further comprising repeating the powering, supplying, sweeping, receiving, selecting, generating and detecting steps while the duty cycle of the power signal is changed for each power frequency.

10. The method according to claim 1, further comprising repeating the powering, supplying, sweeping, receiving, selecting, generating and detecting steps while the duty cycle of the power signal is changed.

11. The method according to claim 1, wherein sweeping the surface comprises sweeping an active surface of the electronic integrated circuit with the laser beam.

12. A method for making an electronic integrated circuit, the method comprising:
 fabricating an integrated circuit that includes a power input and a data input;
 applying a periodic power signal to the power input of the integrated circuit, the periodic power signal having a frequency;
 applying a test signal to the data input of the integrated circuit;
 sweeping a surface of the electronic integrated circuit with a laser beam;
 generating a first image using a laser beam reflected from the surface;
 generating a second image using a selected part of the laser beam reflected from the surface, the selected part of the reflected laser beam having a frequency corresponding to the frequency of the power signal; and
 detecting defects in the integrated circuit by superposing the first image and the second image.

13. A system for detecting defects in an electronic integrated circuit that includes a power input and a data input, the system comprising:
 means for powering the electronic integrated circuit with a periodic power signal having a frequency;
 means for supplying an input signal to the data input;
 means for sweeping a surface of the electronic integrated circuit with a laser beam;
 means for generating a first image using a laser beam from the surface and for generating a second image using a selected part of the reflected laser beam, the selected part having a frequency corresponding to the frequency of the power signal; and
 means detecting defects in the integrated circuit by superposing the first image and the second image.

14. The system according to claim 13, further comprising means for converting information of the laser beam into an electronic signal and providing an electronic signal to the means for generating.

15. A system for detecting defects in an electronic integrated circuit that includes a power input and a data input, the system comprising:
 a periodic signal generator configured to be coupled to the power input;
 an input signal generator configured to be coupled to the data input;
 a laser configured to generate a laser beam;
 a moving mechanism configured to move the laser beam and the electronic integrated circuit relative to each other so as to sweep the laser beam over a surface of the electronic integrated circuit;
 a sensor configured to receive the reflected laser beam and deliver an output signal;
 a frequency analyzer configured to select part of the output signal having a frequency corresponding to the frequency of the power signal; and
 a processor configured to generate a first image using the output signal and a second image using the part of the output signal and to superimpose the first image and the second image.

16. The system according to claim 15, wherein the processor is further configured to detect defects based on the superimposed first and second images.

17. The system according to claim 15, wherein the input signal generator comprises a signal generator that generates a zero or non-zero continuous signal.

18. The system according to claim 17, wherein the input signal generator comprises a signal generator that generates a periodic signal.

19. The system according to claim 18, wherein the frequency of the power signal is different from the frequency of the input signal.

20. The system according to claim 19, wherein the periodic signal generator is configured to deliver a power signal with a frequency that is different from the first five harmonics of the periodic signal delivered by the input signal generator.

21. The system according to claim 15, wherein the periodic signal generator is configured to generate a square-wave signal.

22. The system according to claim 15, wherein the electronic integrated circuit comprises electronic elements and wherein the input signal generator is configured to deliver a power signal having a half-period that is longer than the longest heating time constant of materials of the electronic elements.

23. The system according to claim 15, wherein the input signal generator is configured to generate a periodic signal having a frequency between 10 kHz and 1 MHz.

24. The system according to claim 15, wherein the input signal generator comprises a variable frequency generator.

25. The system according to claim 15, wherein the input signal generator comprises a variable duty-cycle generator.

* * * * *